United States Patent
Bakhite-Al et al.

(10) Patent No.: US 11,384,173 B2
(45) Date of Patent: Jul. 12, 2022

(54) ADDITIVE COMPOSITION

(71) Applicant: SABIC GLOBAL TECHNOLOGIES B.V., Bergen op Zoom (NL)

(72) Inventors: Ali Abdulwahab Bakhite-Al, Geleen (NL); Abderrahman Meddad, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/437,541

(22) PCT Filed: Mar. 18, 2020

(86) PCT No.: PCT/EP2020/057509
§ 371 (c)(1),
(2) Date: Sep. 9, 2021

(87) PCT Pub. No.: WO2020/188002
PCT Pub. Date: Sep. 24, 2020

(65) Prior Publication Data
US 2022/0089792 A1 Mar. 24, 2022

(30) Foreign Application Priority Data
Mar. 21, 2019 (EP) .................... 19164212

(51) Int. Cl.
| C08F 8/50 | (2006.01) |
| C08K 5/098 | (2006.01) |
| C08K 5/14 | (2006.01) |
| C08K 5/3492 | (2006.01) |
| C08K 5/526 | (2006.01) |
| C08K 9/12 | (2006.01) |
| C07C 409/16 | (2006.01) |

(52) U.S. Cl.
CPC .............. C08F 8/50 (2013.01); C07C 409/16 (2013.01); C08K 5/098 (2013.01); C08K 5/14 (2013.01); C08K 5/34926 (2013.01); C08K 5/526 (2013.01); C08K 9/12 (2013.01); C08F 2810/10 (2013.01)

(58) Field of Classification Search
CPC ... C08K 9/12; C08K 5/14; C08K 5/00; C08K 5/098; C08K 5/3492; C08K 5/526; C08F 8/50
See application file for complete search history.

(56) References Cited

U.S. PATENT DOCUMENTS

| 4,900,781 A | 2/1990 | Hirai et al. |
| 2011/0118400 A1 | 5/2011 | Neuteboom et al. |
| 2019/0062527 A1* | 2/2019 | Mizushima ............ C08K 5/098 |

FOREIGN PATENT DOCUMENTS

| EP | 0 264 156 A1 * | 4/1988 | ................ C08F 8/50 |
| EP | 0264156 A1 | 4/1988 | |
| WO | 2010009825 A1 | 1/2010 | |
| WO | WO-2010009825 A1 * | 1/2010 | ................ C08F 8/50 |

OTHER PUBLICATIONS

International Search Report; International Application No. PCT/EP2020/057509; International Filing Date: Mar. 18, 2020; dated Sep. 24, 2020; 5 pages.
Written Opinion; International Application No. PCT/EP2020/057509; International Filing Date: Mar. 18, 2020; dated Sep. 24, 2020; 5 pages.

* cited by examiner

*Primary Examiner* — Robert D Harlan
(74) *Attorney, Agent, or Firm* — Cantor Colburn LLP

(57) ABSTRACT

The invention relates to a composition obtained by the adsorption of a liquid peroxide onto granules comprising an antioxidant and an acid scavenger, for example wherein the adsorption of the liquid peroxide onto the granules is performed by a process which can be performed at room temperature (23° C.) and the process does not require heating.

14 Claims, No Drawings

ADDITIVE COMPOSITION

CROSS REFERENCE TO RELATED APPLICATIONS

This application is a National Stage application of PCT/EP2020/057509, filed Mar. 18, 2020, which claims the benefit of European Application No. 19164212.3, filed Mar. 21, 2019, both of which are incorporated by reference in their entirety herein.

The present invention relates to a composition obtained by the adsorption of a liquid peroxide onto granules comprising an antioxidant and an acid scavenger.

There is a continuous search for methods to modify the rheology of polypropylene, in particular to reduce their viscosity. The viscosity reduction is often also described as "vis-breaking", "melt-shifting", "modifying rheology" or "controlling rheology". It is known that organic peroxides may be used to reduce the viscosity. Several methods of dosage of organic peroxides are known.

One common method of dosage of organic peroxides is to inject a liquid organic peroxide directly into the extruder hopper or to a mixer to be homogenized with polypropylene prior to extrusion without changing plant operating reactor conditions. A typical process consists of mixing liquid peroxide with solid polypropylene powder in a blender before introducing it into the extruder. This allows a quasi-perfect mixing between peroxide and polypropylene. However, this mixing process in the blender adds an additional processing step and does not require any change in the compounding formulation during extrusion.

Solid peroxide compositions are also known. For example, certain mineral fillers with 40 to 45 wt % of absorbed peroxides are known. These solid peroxides have a problem with dosing accuracy and dispersion of the peroxide in the filler.

A further example of a solid peroxide composition comprises porous polypropylene particles with absorbed peroxide. This product requires the use of a specific polypropylene having a high porosity.

A further example of a solid peroxide composition comprises a masterbatch of peroxide in polypropylene. This requires extrusion of the carrier polypropylene at a very low temperature to avoid peroxide decomposition. Moreover, this product is more expensive than absorbed products. This product at higher peroxide dosage is classified as unsafe, and there is legislation constraining its production, handling, transportation, storage and use.

Accordingly, it is an objective of the present invention to provide a peroxide composition in which the above-mentioned and/or other problems are solved.

The invention provides a composition obtained by the adsorption of a liquid peroxide onto granules comprising an antioxidant and an acid scavenger.

The composition according to the invention does not require expensive components and can be made in a simple and cost-efficient manner. Further, the composition according to the invention was found to be stable and safe to handle, store and transport. It was found that the composition according to the invention can be classified as UN3108 (organic peroxide Type E, solid) according to Recommendations on the transport of dangerous goods, Model Regulations, Volume I, United Nations, 20th revised edition, 2017. Thus, the composition according to the invention does not require special containers for transportation and cold warehouses for storages. Further, the composition according to the invention, when used for vis-breaking polypropylene, is homogeneously distributed in the polypropylene during the extrusion. This positively influences the properties of the vis-broken polypropylene.

The composition according to the invention may be classified as Type G according to Recommendations on the transport of dangerous goods, Manual of Tests and Criteria, fifth revised edition, 2009. This means that the composition according to the invention is not subject to the provisions of Class 5.2.

Granules

Additives, for example stabilizers, nucleating agents and anti-static agents are commonly added to polymers. Additives can be used in the form of granules where additives are pre-blended with a carrier resin, e.g. polyethylene, polypropylene.

According to the present invention, the granules comprise only additives and does not comprise a carrier resin.

In the present invention, the term 'granule' refers to a particle with various shapes, e.g. beads, tablets, pellets, pastilles, fragments, flakes and the like. The longest length (straight line measurement) of the granule according to the present invention is for example in the range of 0.05 to 5.00 mm. If the longest length is less than 0.50 mm, the granule is considered to be a dust.

Preferably, the granules according to the present invention is substantially dust-free.

By 'substantially dust-free' is meant that there is little or no dust present in the granules, e.g. there are little or no granules having a longest length of less than 0.5 mm. For example, the amount of dust may be less than 15.0 wt %, less than 10.0 wt %, less than 5.0 wt %, less than 2.0 wt %, less than 1.0 wt %, less than 0.75 wt %, less than 0.50 wt %, less than 0.25 wt %, less than 0.10 wt %, less than 0.075 wt %, less than 0.050 wt %, less than 0.025 wt %, less than 0.010 wt % or 0 wt % based on the total weight of granules. A low level of dust in the additive granules is advantageous in terms of environmental health and safety. In particular, a low level of dust reduces the likelihood that personnel will inhale potentially harmful dust particles.

The adsorption of the liquid peroxide onto the granules is performed by a process wherein the process which can be performed at room temperature (23° C.) and the process does not require heating.

Preferably, the adsorption of the liquid peroxide onto the granules is performed by a cold compaction process or a cold extrusion process.

In a cold compaction process, the liquid peroxide and the granules are first homogenized mechanically with mainly shear stress, then the mixture of liquid peroxide and granules is pressed into the desired shape, e.g. pellet, disk. No heating device is required during the cold compaction process.

In a cold extrusion process, the liquid peroxide and the granules are mixed and extruded without heating. Homogeneous adsorption of the liquid peroxide on the granules can be achieved by the compressive and shear stress during the cold extrusion process.

The granules comprise an antioxidant and an acid scavenger. The granules may further comprise other additives such as a slip agent and an anti-blocking agent.

Preferably, the total amount of the antioxidant and the acid scavenger is at least 50 wt %, for example at least 60 wt %, at least 70 wt %, at least 80 wt % or at least 90 wt %, with respect to the granules. Preferably, the granules substantially consists of the antioxidant and the stearate, i.e. the total amount of the antioxidant and the stearate is at least 95 wt %, at least 98 wt %, at least 99 wt % with respect to the granules.

Preferably, the amount of the antioxidant in the composition is 50 to 85 wt %, e.g. 60 to 85 wt % or 70 to 80 wt %, with respect to the total composition.

Preferably, the antioxidant present in the solid composition is a phenolic antioxidant and/or an organic phosphite or phosphonite. Preferably, the antioxidant present in the solid composition is a phenolic antioxidant and an organic phosphite or phosphonite Preferably, the amount of the phenolic antioxidant in the solid composition is 10 to 35 wt %, e.g. 15 to 35 wt % or 15 to 25 wt %, with respect to the total composition.

Preferably, the amount of the organic phosphite or phosphonite in the solid composition is 30 to 60 wt %, e.g. 40 to 55 wt %, with respect to the total composition.

Preferably, the amount of the stearate in the solid composition is 15 to 50 wt %, e.g. 15 to 40 wt % or 20 to 30 wt %, with respect to the total composition.

In particularly preferred embodiments, the amount of the phenolic antioxidant in the composition is 10 to 35 wt %, the amount of the organic phosphite or phosphonite in the composition is 30 to 60 wt % and the amount of the acid scavenger in the composition is 15 to 50 wt %.

Liquid Peroxide

A liquid peroxide is a peroxide or a diluted peroxide that is liquid at room temperature (23° C.).

The liquid peroxide may be present in the composition of the invention in diluted or in undiluted form. If used in diluted form, the liquid diluent in the diluted peroxide can for example be water, methanol, diethylene glycol bis(allyl carbonate), mineral oil, mineral spirits, isoparaffin or a mixture thereof.

Depends on the chemical nature of the peroxide and the type of diluent, the amount of the liquid peroxide is in the range from 30.0 wt % to 99.9 wt % based on the total amount of the diluted peroxide.

Even more preferably, the liquid peroxide is DHRP.

Preferably, the amount of the liquid peroxide in the composition is 1 to 30 wt %, for example 3 to 20 wt % or 5 to 15 wt % with respect to the total composition.

Phenolic Antioxidant

A phenolic antioxidant is sometimes also called a primary antioxidant.

Preferably the phenolic antioxidant is a compound of the formula (I)

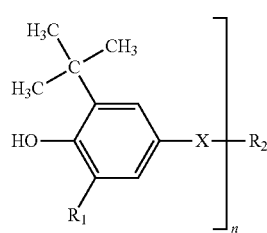
(I)

in which
$R_1$ is $C_1$-$C_4$ alkyl,
n is 1, 2, 3 or 4,

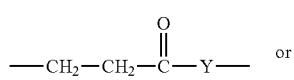 or

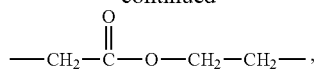

X is methylene, or
Y is hydrogen or —NH—; and,
if n is 1,
X is

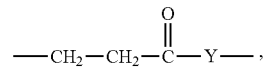

where Y is attached to $R_2$, and
$R_2$ is $C_1$-$C_{25}$ alkyl; and,
if n is 2,
X is

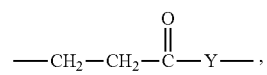

where Y is attached to $R_2$, and
$R_2$ is $C_2$-$C_{12}$ alkylene, $C_4$-$C_{12}$ alkylene interrupted by oxygen or sulfur; or, if Y is —NH—,
$R_2$ is additionally a direct bond; and,
if n is 3,
X is methylene or

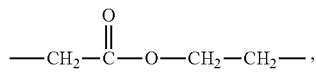

where the ethylene group is attached to $R_2$, and
$R_2$ is

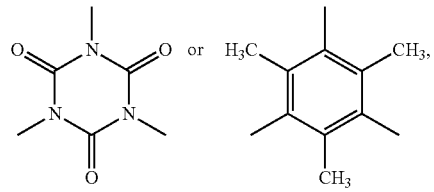

and
if n is 4,
X is

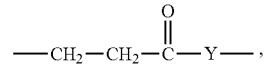

where Y is attached to $R_2$, and
$R_2$ is $C_4$-$C_1$ alkanetetrayl.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. A preferred definition of $R_1$ is methyl and tert-butyl. A particularly preferred definition of $R_2$ is $C_1$-$C_{20}$ alkyl, especially $C_1$-$C_{18}$ alkyl, for example $C_4$-$C_{18}$ alkyl. An especially preferred definition of $R_2$ is $C_8$-$C_{18}$ alkyl, especially $C_{14}$-$C_{18}$ alkyl, for example $C_{18}$ alkyl.

$C_2$-$C_{12}$ alkylene is a branched or unbranched radical, for example ethylene, propylene, tetramethylene, pentamethylene, hexamethylene, heptamethylene, octamethylene, decamethylene or dodecamethylene. A preferred definition of $R_2$ is, for example, $C_2$-$C_{10}$ alkylene, especially $C_2$-$C_8$ alkylene. An especially preferred definition of $R_2$ is, for example, $C_4$-$C_8$ alkylene, especially $C_4$-$C_6$ alkylene, for example hexamethylene. $C_4$-$C_{12}$ alkylene interrupted by oxygen or sulfur can be interrupted one or more times and is, for example, —$CH_2$—O—$CH_2CH_2$—O—$CH_2$—, —$CH_2$—(O—$CH_2CH_2$-)$_2$O—$CH_2$—, —$CH_2$—(O—$CH_2CH_2$-)$_3$O—$CH_2$—, —$CH_2$—(O—$CH_2CH_2$-)$_4$O—$CH_2$—, —$CH_2CH_2$—O—$CH_2CH_2$—O—$CH_2CH_2$— or —$CH_2CH_2$—S—$CH_2CH_2$—. A preferred definition of $R_2$ is, for example, $C_4$-$C_{10}$ alkylene interrupted by oxygen or sulfur, especially $C_4$-$C_8$ alkylene interrupted by oxygen or sulfur, for example $C_4$-$C_{18}$ alkylene interrupted by oxygen or sulfur. An especially preferred meaning of $R_2$ is —$CH_2CH_2$—O—$CH_2CH_2$—O—$CH_2CH_2$— or —$CH_2CH_2$—S—$CH_2CH_2$—.

Alkanetetrayl having 4 to 10 carbon atoms is, for example,

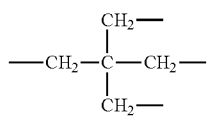

(pentaerythrityl)

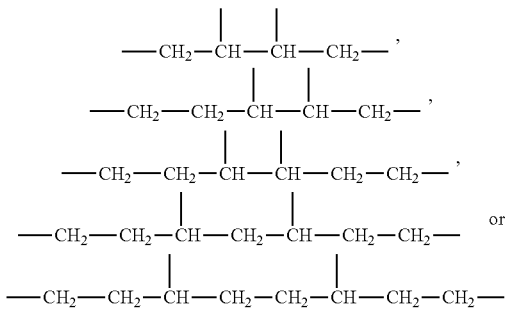

Pentaerythrityl is preferred.

The phenolic antioxidant may also comprise mixtures of different sterically hindered phenols of the formula I.

An example of a suitable phenolic antioxidant is a compound of the formula I in which,
if n is 1, $R_2$ is $C_1$-$C_{20}$ alkyl.

A further example of a suitable phenolic antioxidant is a compound of the formula I in which, if n is 2,
$R_2$ is $C_2$-$C_8$ alkylene, $C_4$-$C_8$ alkylene interrupted by oxygen or sulfur; or, if Y is —NH—, $R_2$ is additionally a direct bond; and, if n is 3,
X is methylene,
$R_2$ is

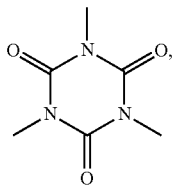

and,
if n is 4,
$R_2$ is $C_4$-$C_8$ alkanetetrayl.

A further example of a suitable phenolic antioxidant is a compound of the formula I in which
$R_1$ is methyl or tert-butyl, n is 1, 2, 3 or 4,
X is methylene or

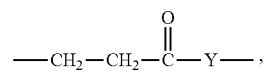

Y is hydrogen or —NH—; and,
if n is 1,
$R_2$ is $C_{14}$-$C_{18}$ alkyl; and
if n is 2,
$R_2$ is $C_4$-$C_6$ alkylene, or is $C_4$-$C_6$ alkylene interrupted by oxygen; and,
if n is 3,
X is methylene,
$R_2$ is

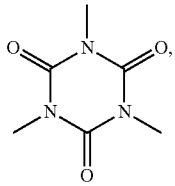

and,
if n is 4,
$R_2$ is $C_4$-$C_6$ alkanetetrayl.

A further example of a suitable phenolic antioxidant is a compound of the formula I in which the compound of the formula (1) is a compound of the formula (Ia) to (Ii)

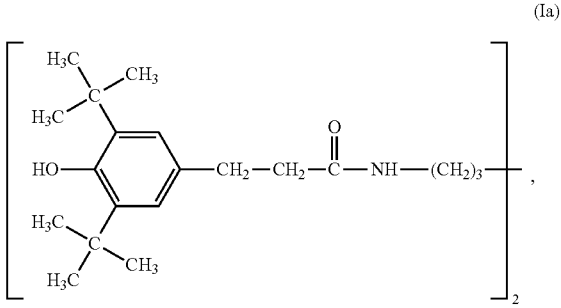

Irganox® 1098

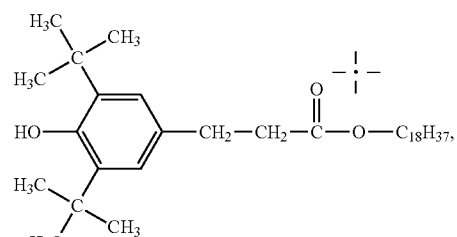

Irganox®1076 (Ib)

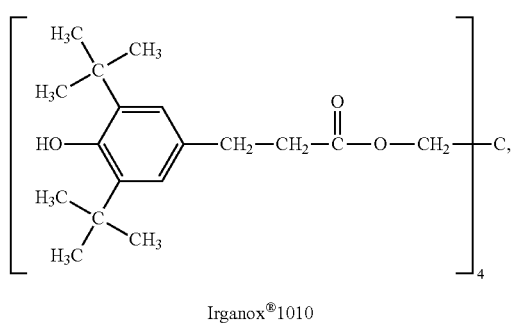

Irganox®1010 (Ic)

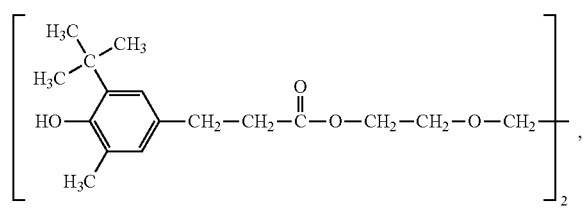

Irganox® 245 (Id)

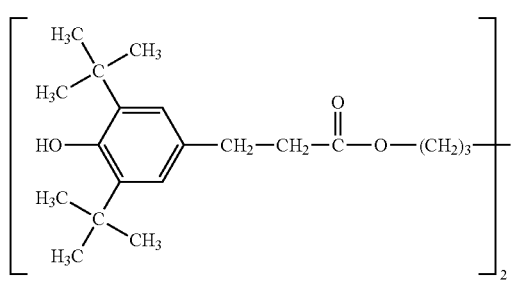

Irganox® 259 (Ie)

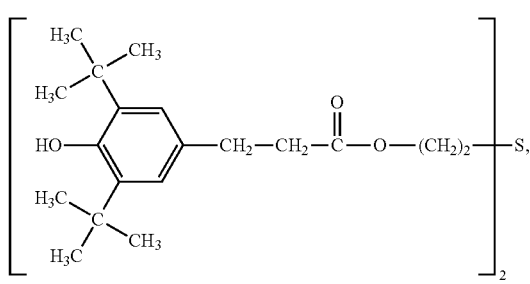

Irganox® 1035 (If)

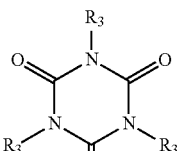

Irganox® 3114 (Ig)

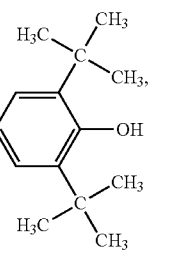

$R_3 = $ —$CH_2$—

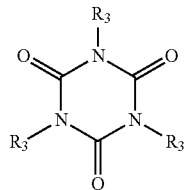

Irganox® 3125 (Ih)

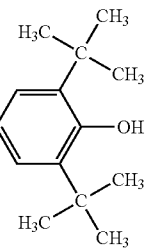

$R_3 = $ —$(CH_2)_2$—O—

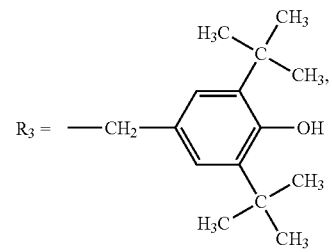

Irganox® 1330 (Ii)

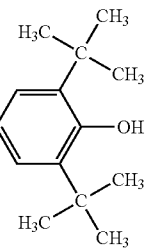

$R_3 = $ —$CH_2$—

Irganox®1098, Irganox®1076, Irganox®1010, Irganox®245, Irganox®259, Irganox®3114, Irganox®1035, Irganox®3125 and Irganox®1330 are protected trade names of Ciba Inc. A suitable phenolic antioxidant having the same structure as Irganox® 3114 is also available as SONG-NOX® 3114 from Songwon.

Organic Phosphite and Phosphonite

Organic phosphite and phosphonite function as a processing stabilizer and are also sometimes called a secondary antioxidant.

Specifically, the organic phosphites or phosphonites may mean compounds of the formulae (II) to (VIII)

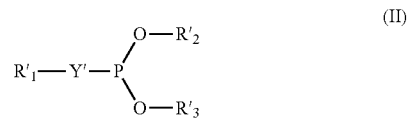

(II)

-continued

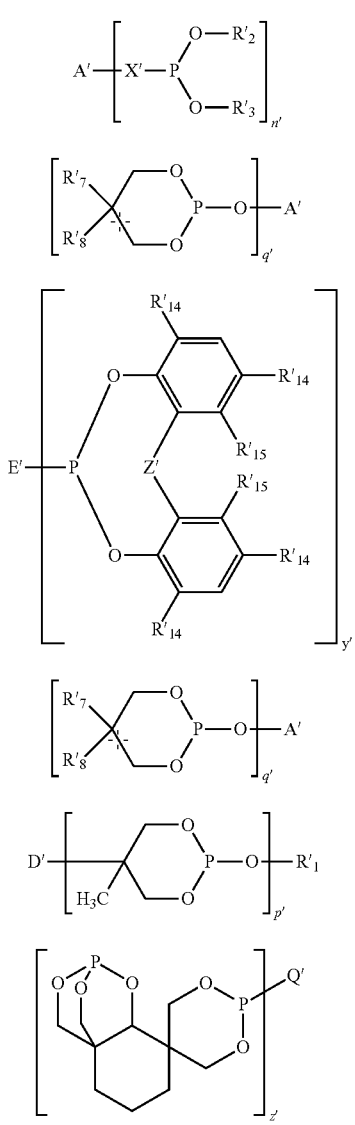

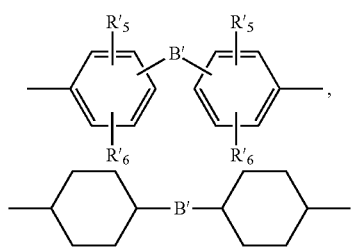

or phenylene;

A', if n' is 3, is a radical of the formula —$C_{r'}H_{2r'-1}$;

A', if n' is 4,

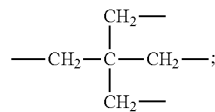

(III)

(VI)

(V)

(VI)

(VII)

(VIII)

A" has the meaning of A' if n' is 2;

B' is a direct bond, —$CH_2$—, $CHR'_4$—, —$CR'_1R'_4$—, sulfur or $C_5$-$C_7$ cycloalkylidene, or cyclohexylidene substituted by from 1 to 4 $C_1$-$C_4$ alkyl radicals in position 3, 4 and/or 5;

D', if p' is 1, is methyl and, if p' is 2, is —$CH_2OCH_2$—;

E', if y' is 1, is $C_1$-$C_{18}$ alkyl, —$OR'_1$ or halogen;

E', if y is 2, is —O-A"-O—,

E', if y is 3, is a radical of the formula $R'_4C(CH_2O—)_3$ or $N(CH_2CH_2O—)_3$;

Q' is the radical of an at least z'-valent alcohol or phenol, this radical being attached via the oxygen atom to the phosphorus atom;

$R'_1$, $R'_2$ and $R'_3$ independently of one other are unsubstituted or halogen, —$COOR_4'$. —CN— or —$CONR_4'R_4'$-substituted $C_1$-$C_{18}$ alkyl; $C_2$-$C_{18}$ alkyl interrupted by oxygen, sulfur or —$NR'_4$—; $C_7$-$C_9$ phenylalkyl; $C_5$-$C_{12}$ cycloalkyl, phenyl or naphthyl; naphthyl or phenyl substituted by halogen, 1 to 3 alkyl radicals or alkoxy radicals having in total 1 to 18 carbon atoms or by $C_7$-$C_9$phenylalkyl; or are a radical of the formula

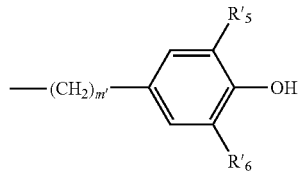

in which m' is an integer from the range 3 to 6;

$R'_4$ is hydrogen, $C_1$-$C_{18}$ alkyl, $C_5$-$C_{12}$ cycloalkyl or $C_7$-$C_9$ phenylalkyl, $R'_5$ and $R'_6$ independently of one another are hydrogen, $C_1$-$C_8$ alkyl or $C_5$-$C_6$ cycloalkyl, $R'_7$ and $R'_8$, if q' is 2, independently of one another are $C_1$-$C_4$ alkyl or together are a 2,3-dehydropentamethylene radical; and $R'_7$ and $R'_8$, if q' is 3, are methyl;

$R'_{14}$ is hydrogen, CC alkyl or cyclohexyl, $R'_{15}$ is hydrogen or methyl and, if two or more radicals $R'_{14}$ and $R'_{15}$ are present, these radicals are identical or different, X' and Y' are each a direct bond or oxygen, Z' is a direct bond, methylene, —$C(R'_{16})_2$- or sulfur, and $R'_{16}$ is $C_1$-$C_8$ alkyl.

Typical examples of the organic phosphite or phosphonite are:

Triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite (Irgafos® 168, Ciba Specialty Chemicals Inc.; SONG-NOX®1680), diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bisisodecyloxy-pentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis(2,4-di-tert-butylphenyl) 4,4'-biphenylenediphosphonite (Irgafos®P-EPQ, Ciba Specialty Chemicals Inc.), 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyldibenzo[d,g]-1,3,2-dioxaphosphocin, bis(2,4-di-tert-butyl-6-methylphenyl) methyl phosphite, bis(2,4-di-tert-butyl-6-methylphenyl) ethyl phosphite.

The above mentioned organic phosphites and phosphonites are known compounds; many of them are available commercially.

In particularly preferred embodiments, the antioxidant present in the solid composition is 1,3,5-Tris(3,5-di-tert-butyl-4-hydroxybenzyl)-1,3,5-triazinane-2,4,6-trione and tris(2,4-di-tert-butylphenyl) phosphite.

Acid Scavenger

It is common that there exists a small amount of catalyst residue in the freshly produced propylene-based polymer, acid scavenger is often used to neutralize the acidity of the catalyst residue.

The acid scavenger can for example be an inorganic acid scavenger, e.g. a basic inorganic salt or an organic acid scavenger.

Preferably, the acid scavenger is an organic acid scavenger.

More preferably, the organic acid scavenger is a stearate selected from the group consisting of calcium stearate, zinc stearate, magnesium stearate and/or a mixture thereof. Most preferably, the stearate is calcium stearate.

Method for Viscosity Breaking

The present invention further provides a method for viscosity breaking of a propylene-based polymer, comprising adding the solid composition according to the invention to the propylene-based polymer and heating the resultant composition, e.g. by melt-mixing.

The conditions of the heating or melt-mixing, such as the temperature and the duration, are selected so that a propylene-based polymer having a desired melt flow index is obtained. Suitable conditions for melt-mixing, such as temperature, pressure, amount of shear, screw speed and screw design when an extruder is used are known to the skilled person.

Propylene-Based Polymer

The propylene-based polymer subjected to the method for viscosity breaking may for example be a propylene homopolymer or a random propylene-α-olefin copolymer or a heterophasic propylene copolymer.

The propylene-based polymer to be subjected to the method for viscosity breaking may have a melt flow index (MFI) as measured according to ISO1133-1:2011 (2.16 kg/230° C.) of e.g. 0.1 to 100 dg/min.

The propylene-based polymer after being subjected to the method for viscosity breaking has a MFI higher than that of the propylene-based polymer to be subjected to the method for viscosity breaking. For example, after viscosity breaking the propylene based polymer may have a MFI as measured according to ISO1133-1:2011 (2.16 kg/230° C.) of 1 to 200 dg/min.

A propylene homopolymer can be obtained by polymerizing propylene under suitable polymerization conditions. A propylene copolymer can be obtained by copolymerizing propylene and one or more other α-olefins, preferably ethylene, under suitable polymerization conditions. The preparation of propylene homopolymers and copolymers is, for example, described in Moore, E. P. (1996) Polypropylene Handbook. Polymerization, Characterization, Properties, Processing, Applications, Hanser Publishers: New York.

The α-olefin in the random propylene α-olefin copolymer is for example an α-olefin chosen from the group of α-olefins having 2 or 4 to 10 C-atoms, preferably ethylene, 1-butene, 1-hexene or any mixtures thereof. The amount of α-olefin is preferably at most 10 wt % based on the propylene α-olefin copolymer, for example in the range from 2-7 wt % based on the propylene α-olefin copolymer.

Polypropylenes can be made by any known polymerization technique as well as with any known polymerization catalyst system. Regarding the techniques, reference can be given to slurry, solution or gas phase polymerizations; regarding the catalyst system reference can be given to Ziegler-Natta, metallocene or single-site catalyst systems. All are, in themselves, known in the art.

Heterophasic propylene copolymers are generally prepared in one or more reactors, by polymerization of propylene in the presence of a catalyst and subsequent polymerization of a propylene-α-olefin mixture. The resulting polymeric materials are heterophasic, but the specific morphology usually depends on the preparation method and monomer ratio.

The heterophasic propylene copolymer as defined herein comprises of a propylene-based matrix and a dispersed ethylene-α-olefin copolymer.

The propylene-based matrix typically forms the continuous phase in the heterophasic propylene copolymer.

The propylene-based matrix for example consists of a propylene homopolymer and/or a propylene-α-olefin copolymer consisting of at least 70% by mass of propylene and up to 30% by mass of α-olefin, for example ethylene, for example consisting of at least 80% by mass of propylene and up to 20% by mass of α-olefin, for example consisting of at least 90% by mass of propylene and up to 10% by mass of α-olefin, based on the total mass of the propylene-based matrix.

For example, the α-olefin in the propylene-α-olefin copolymer is selected from the group of α-olefins having 2 or 4-10 carbon atoms and is preferably ethylene. For example, the propylene-based matrix consists of a propylene homopolymer.

The melt flow index (MFI) of the propylene-based matrix (before it is mixed into the composition of the invention) may be in the range of for example 0.3 to 200 dg/min as measured according to ISO1133 (2.16 kg/230° C.).

The propylene-based matrix is for example present in an amount of 50 to 85 wt % based on the total heterophasic propylene copolymer.

Besides the propylene-based matrix, the heterophasic propylene copolymer also consists of a dispersed ethylene-α-olefin copolymer. The dispersed ethylene-α-olefin copolymer is also referred to herein as the 'dispersed phase'. The dispersed phase is embedded in the heterophasic propylene copolymer in a discontinuous form.

The MFI of the dispersed ethylene α-olefin copolymer may vary between wide range and may for example be in the range from for example be in the range from 0.001 to 10 dg/min (measured according to ISO1133 (2.16 kg/230° C. as calculated using the following formula:

$$MFI\ EPR = 10^{\wedge}\left(\frac{\text{Log } MFI \text{ heterophasic} - \text{matrix content} * \text{Log } MFI\ PP}{\text{rubber content}}\right)$$

wherein MFI heterophasic is the melt flow rate of the heterophasic propylene copolymer measured according to ISO1133-1 (2011) (2.16 kg/230° C.), MFI PP is the MFR of the propylene-based matrix of the heterophasic propylene copolymer measured according to ISO1133-1 (2011) (2.16 kg/230° C.), matrix content is the amount of propylene-based matrix in the heterophasic propylene copolymer in wt % and rubber content is the amount of ethylene α-olefin copolymer in the heterophasic propylene copolymer in wt %.

The dispersed ethylene-α-olefin copolymer is for example present in an amount of 50 to 15 wt % based on the total heterophasic propylene copolymer.

For example, the amount of ethylene in the ethylene-α-olefin copolymer (RCC2) is in the range of 20-65 wt % based on the ethylene-α-olefin copolymer.

The amounts of the propylene-based matrix and the dispersed ethylene-α-olefin copolymer, as well as the amount of ethylene in the ethylene α-olefin copolymer may be determined by $^{13}$C-NMR, as is well known in the art.

In the heterophasic polypropylene, the sum of the total weight of the propylene-based matrix and the total weight of the dispersed ethylene-α-olefin copolymer is 100 wt % The α-olefin in the ethylene-α-olefin copolymer is for example chosen from the group of α-olefins having 3 to 8 carbon atoms and any mixtures thereof, for example the α-olefin in the ethylene-α-olefin copolymer is chosen from the group of α-olefins having 3 to 4 carbon atoms and any mixture thereof, for example the α-olefin is propylene, in which case the ethylene-α-olefin copolymer is ethylene-propylene copolymer. Examples of suitable α-olefins having 3 to 8 carbon atoms, which may be employed as ethylene comonomers to form the ethylene α-olefin copolymer include but are not limited to propylene, 1-butene, 1-pentene, 4-methyl-1-pentene, 1-hexen, 1-heptene and 1-octene.

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

When values are mentioned for a lower limit and an upper limit for a parameter, ranges made by the combinations of the values of the lower limit and the values of the upper limit are also understood to be disclosed.

The invention is now elucidated by way of the following examples, without however being limited thereto.

Solid Additive Composition

A solid additive composition was obtained by the adsorption of 2,5 Dimethyl 2,5 Di(tert-butylperoxy) hexane by a cold compaction process onto granules consisting of 1,3,5-Tris(3,5-di-tert-butyl-4-hydroxybenzyl)-1,3,5-triazinane-2,4,6-trione, tris(2,4-di-tert-butylphenyl) phosphite and calcium stearate. The resulting solid additive composition had components as shown in Table 1.

TABLE 1

|  | Amount (wt %) |
| --- | --- |
| 2,5 Dimethyl 2,5 Di(tert-butylperoxy) hexane | 10 |
| 1,3,5-Tris(3,5-di-tert-butyl-4-hydroxybenzyl)-1,3,5-triazinane-2,4,6-trione | 23.3 |
| tris(2,4-di-tert-butylphenyl) phosphite | 46.4 |
| Calcium stearate | 20.3 |

A product safety investigation consisting of the following tests was performed on the solid additive composition.
Differential Scanning Calorimeter (DSC)
Spatula test
BAM impact hammer test
Friction tests
Pressure vessel test (PVT) (exploratory)
Ignition tests
Visual decomposition temperature
Evaporation/concentration test
Further a thermal stability test (mini-Heat Accumulation Storage Test) was performed on the solid additive composition.

The investigation revealed no safety issues. The composition can be handled, stored and transported safely. According to the results, the composition was classified as UN3108 (organic peroxide Type E, solid) according to Recommendations on the transport of dangerous goods, Model Regulations, Volume I, United Nations, 20th revised edition, 2017.

Visbreaking

EXAMPLE 1

The solid additive composition was added to a polypropylene homopolymer having a melt flow index of 1.78 dg/min (ISO1133:1-2011, 230° C. and 2.16 kg) such that the amounts of Trigonox 101 dosed with respect to the total composition are as shown in Table 2 and the resulting composition was extruded at a temperature setting of 190/225/225/228/228/230° C. The MFI reached is summarized in Table 2.

TABLE 2

| Ex | Amount of Trigonox 101 (wt %) | MFI reached (dg/min) |
| --- | --- | --- |
| 1 | 0 | 1.78 |
| 2 | 0.055 | 16.8 |
| 3 | 0.081 | 29.5 |
| 4 | 0.097 | 37.9 |
| 5 | 0.146 | 64.5 |

As can be seen, the composition of the invention while having a type E safety classification, is capable of visbreaking polypropylene.

The invention claimed is:
1. A composition obtained by the adsorption of a liquid peroxide onto granules comprising an antioxidant and an acid scavenger.
2. The composition according to claim 1, wherein the adsorption of the liquid peroxide onto the granules is performed by a process which is performed at room temperature and without heating.

3. The composition according to claim 1 wherein the adsorption of the peroxide onto the granules is performed by a compaction process or by a cold extrusion process.

4. The composition according to claim 1, wherein the total amount of the antioxidant and the acid scavenger is at least 50 wt % with respect to the granules.

5. The composition according to claim 1, wherein the acid scavenger is a stearate.

6. The composition according to claim 1, wherein the amount of the antioxidant in the solid composition is 50 to 85 wt % with respect to the total solid composition and the amount of the stearate is 15 to 50 wt % with respect to the total composition.

7. The composition according to claim 1, wherein the amount of the liquid peroxide in the solid composition is 1 to 30 wt % with respect to the total composition.

8. The composition according to claim 1, wherein the liquid peroxide is 2,5 Dimethyl 2,5 Di(tert-butylperoxy) hexane.

9. The composition according to claim 1, the antioxidant present in the composition is at least one of a phenolic antioxidant, an organic phosphite, or an organic phosphonite.

10. The composition according to claim 9, wherein the amount of the phenolic antioxidant in the solid additive composition is 10 to 35 wt % with respect to the solid additive composition and/or the amount of the organic phosphite or phosphonite in the solid additive composition is 30 to 60 wt % with respect to the composition.

11. The composition according to claim 1, wherein the antioxidant present in the solid composition is 1,3,5-Tris(3,5-di-tert-butyl-4-hydroxybenzyl)-1,3,5-triazinane-2,4,6-trione and tris(2,4-di-tert-butylphenyl) phosphite.

12. The composition according to claim 1, wherein the acid scavenger is selected from the group consisting of calcium stearate, zinc stearate, magnesium stearate and/or a mixture thereof.

13. The composition according to claim 1, wherein the composition is classified as UN3108 (organic peroxide Type E, solid) according to Recommendations on the transport of dangerous goods, Model Regulations, Volume I, United Nations, 20th revised edition, 2017.

14. A method for viscosity breaking of a propylene-based polymer, comprising adding the composition according to claim 1 to the propylene-based polymer and heating the resultant composition.

* * * * *